(12) United States Patent
Gray et al.

(10) Patent No.: US 6,605,071 B1
(45) Date of Patent: Aug. 12, 2003

(54) TODDLER'S DISPOSABLE/REUSABLE GARMENT WITH UNIVERSAL DISPOSABLE LINER/DIAPER

(76) Inventors: Vivian Gray, 3600 Wyntering Trail, Marietta, GA (US) 30068; Pamela G. deMonye, 383 Bridgebrook La., Smyrna, GA (US) 30082

( * ) Notice: Subject to any disclaimer, the term of this patent is extended or adjusted under 35 U.S.C. 154(b) by 1121 days.

(21) Appl. No.: 08/931,080

(22) Filed: Sep. 15, 1997

Related U.S. Application Data

(63) Continuation of application No. 08/675,578, filed on Jul. 3, 1996, now abandoned.

(51) Int. Cl.$^7$ .......................... A61F 13/15; A61F 13/20; A41B 9/04
(52) U.S. Cl. .......................... 604/385.28; 604/385.03; 604/385.14; 604/387; 604/395; 604/385.01; 2/408
(58) Field of Search ............................... 604/385.1, 402, 604/385.14, 385.03, 385.28, 385.01; 602/67–68, 73; 2/78.1, 80, 400–408

(56) References Cited

U.S. PATENT DOCUMENTS

| | | | | |
|---|---|---|---|---|
| 972,288 A | * | 10/1910 | Taylor | 604/397 |
| 1,188,223 A | * | 6/1916 | Uyeda | 604/394 |
| 1,217,014 A | * | 2/1917 | Knieriem | 604/397 |
| 1,288,848 A | * | 12/1918 | Dudley | 604/397 |
| 1,580,464 A | * | 4/1926 | Blumenfeld | 604/398 |
| 1,977,604 A | * | 10/1934 | Alsop | 604/397 |
| 2,295,016 A | * | 9/1942 | Scribner | 604/397 |
| 2,382,477 A | * | 8/1945 | Goodman et al. | 2/408 |
| 2,481,351 A | * | 9/1949 | Rosenfield | 604/399 |
| 2,597,587 A | * | 5/1952 | Lustgarten | 2/408 |
| 2,705,957 A | * | 4/1955 | Mauro | 604/395 |
| 2,749,912 A | * | 6/1956 | Teitler | 604/395 |
| 2,838,048 A | * | 6/1958 | Kowalski | 604/387 |
| 3,145,394 A | * | 8/1964 | Melton | 2/406 |
| 3,769,979 A | * | 11/1973 | Freney | 604/387 |
| 4,022,212 A | * | 5/1977 | Lovison | 604/398 |
| 4,044,769 A | * | 8/1977 | Papajohn | 604/397 |
| 4,637,078 A | * | 1/1987 | Southwell | 2/408 |
| 4,846,825 A | * | 7/1989 | Enloe et al. | 604/385.2 |
| 4,892,598 A | * | 1/1990 | Stevens et al. | 604/385.2 |
| 5,069,672 A | | 12/1991 | Wippler et al. | 604/385 |
| 5,069,678 A | | 12/1991 | Yamamoto et al. | 604/385 |
| 5,087,253 A | * | 2/1992 | Cooper | 604/385.1 |
| 5,171,239 A | | 12/1992 | Igaue et al. | 604/385 |
| 5,217,447 A | * | 6/1993 | Gagnon | 604/391 |
| 5,290,270 A | | 3/1994 | Fisher | 604/387 |
| 5,445,628 A | * | 8/1995 | Gipson et al. | 604/392 |
| 5,549,593 A | * | 8/1996 | Ygge et al. | 604/392 |

FOREIGN PATENT DOCUMENTS

| | | | | |
|---|---|---|---|---|
| AU | 113113 | * | 5/1941 | 604/481 |
| AU | 652319 | * | 8/1994 | 604/391 |
| CH | 562013 | * | 5/1975 | 2/400 |
| DE | 2648932 | * | 5/1978 | 604/396 |
| FR | 653177 | * | 3/1929 | 604/395 |
| FR | 8615652 | * | 7/1988 | |
| FR | 2679740 | * | 2/1993 | 2/400 |
| WO | 9103220 | * | 3/1991 | 604/385.1 |
| WO | 95/02382 | * | 1/1995 | 604/396 |

* cited by examiner

*Primary Examiner*—Karin Reichle
(74) *Attorney, Agent, or Firm*—Thomas, Kayden, Horstemeyer & Risley

(57) ABSTRACT

A toddler's disposable or reusable garment (10) includes "brief looking" undergarments (12) with a releasable panel (18) that extends down from the back of the waistband (16), through the crotch, and upward for connection to the top front of the waist structure of the undergarment. An absorbent disposable liner/diaper (14) of hourglass configuration is placed in overlying relationship with respect to the releasable panel (18), and the upper end portion (36) of the releasable panel and is connected in underlying relationship with respect to the top front panel 28, allowing the parent to have expedient access to the absorbent disposable liner/diaper for the convenience of changing the liner/diaper without requiring the removal of the garment from about the waist of the toddler.

6 Claims, 3 Drawing Sheets

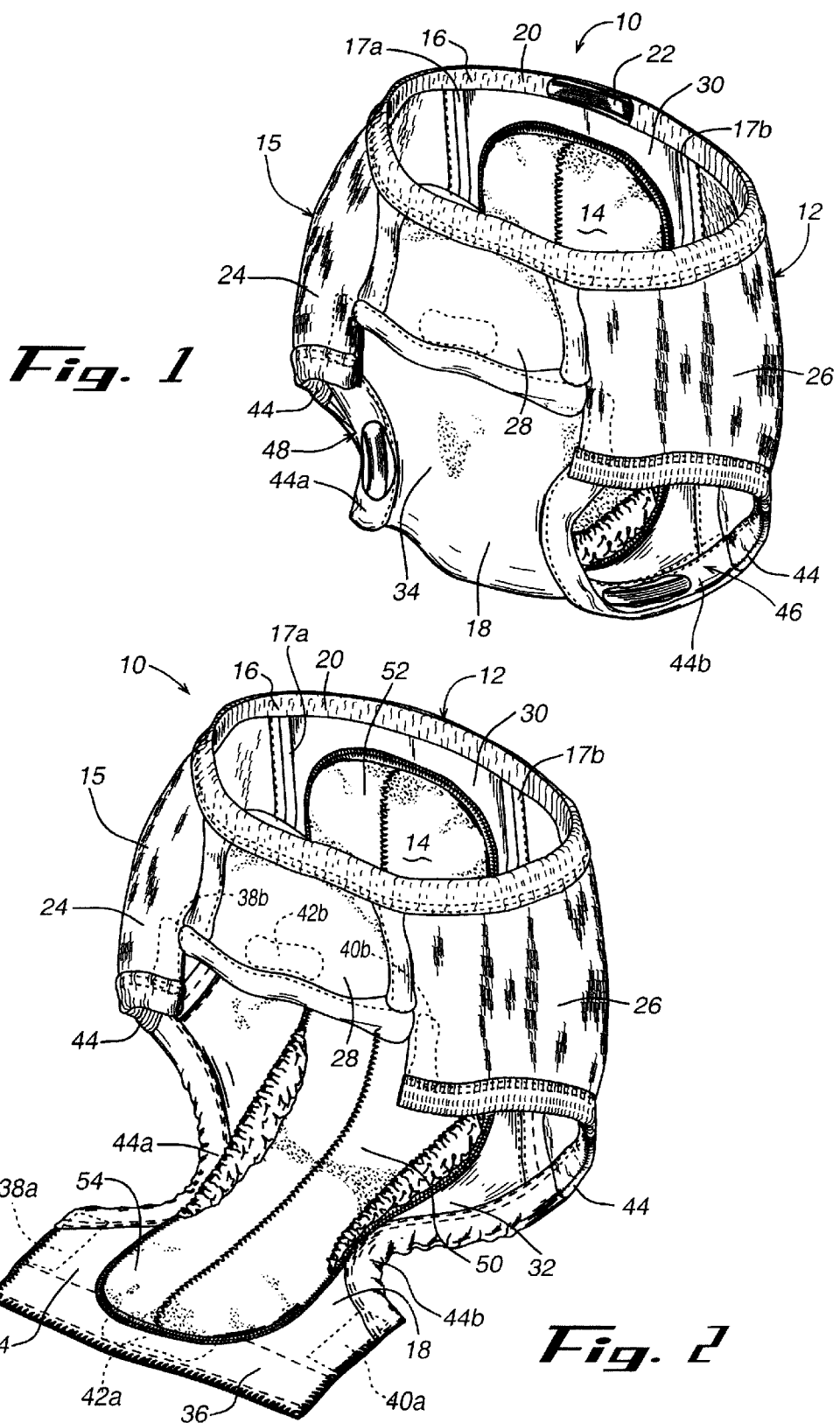

TODDLER'S DISPOSABLE/REUSABLE GARMENT WITH UNIVERSAL DISPOSABLE LINER/DIAPER

This application is a continuation of Application Serial No. 08/675,578, filed Jul. 3, 1996, now abandoned.

FIELD OF THE INVENTION

This invention relates to a garment for an incontinent person, such as a toddler or a child who has learned to walk but has not yet become toilet trained. The garment includes training pants or briefs usually worn as an undergarment about the lower abdomen and a disposable absorbent liner supported in the briefs for receiving and holding body urine and excrement.

BACKGROUND OF THE INVENTION

During the early years of a child's life, when the child is capable of walking, but has not yet become toilet trained, is mobile, social and somewhat communicative, the child is capable of various social functions so, therefore, travels with parents or other responsible adults. Typically, the child travels away from the home in an automobile to various locations, such as to other homes, but also to uncontrolled social environments, such as to a grocery store, to restaurants, to public events and to nursery schools. During these activities, it is not unusual for the toddler to have a bowel movement or urinate.

Typically, the child is dressed in an undergarment, with liquid impervious briefs worn about the outside of the garment, with other external clothing, such as overalls, pants or a dress worn outside the briefs. When the undergarments of a toddler must be changed, the typical situation is that the lower clothing must be completely removed from the lower abdomen of the child in order to gain access to the undergarments and replace them.

A typical diaper still in use today comprises a rectangular-shaped cotton reusable diaper which is usually folded into somewhat of a triangular shape, and is arranged to encircle the waist of the infant or toddler while extending through the crotch area. The newer, more popular diaper for infants or small children is the disposable diaper which has the typical "wing," flat design and is form fitted so as to fasten about the waist of the child, forming leg openings, and providing absorbent material adjacent the lower abdomen of the child while providing a liquid impervious outer layer to block liquids from escaping from the diaper.

Products available in the market for the toilet training cycle of a toddler or a small child include regular cotton reusable garments, or disposable training garments. These products have not met the needs of the consumer during the "in-between" stages. Most parents use a combination of all of the above mentioned products, but all methods available in the market today are messy, or frustrating to the toddler and to the parent when a "diaper change" is made. Some of these products are extremely expensive.

The cotton reusable products offered in the market require the toddler or small child to wear a hot, uncomfortable vinyl pant to protect the other clothing from being soiled. If the toddler or small child has problems with irritation, and is sensitive to the vinyl pant, it can cause skin rashes. When this occurs, the parent is forced to use the cotton training pant alone; causing messy accidents, additional soiled clothing, and making it impossible to remove the undergarment without smearing body excrement everywhere. Adequate "cleanup" is almost impossible in a public facility.

The child may become traumatized by the excrement removal procedure, causing him to regress in the training process. When this happens, it ruins the pleasure of taking the child outside the home for fun and recreation. In order to remove the reusable product from the toddler and change into a clean garment, all clothing must be removed from the toddler from the waist down.

Eliminating unnecessary stress to the toddler during the, changing and cleanup process of the toilet training phase is very important. When trauma is eliminated, the toddler or small child is more likely to relax, and the toilet training program is likely to be more rewarding for both parent and child.

The disposable products currently on the market for toddler or small children make "clean-up" easier, however, changing to a clean garment, as described above, is extremely bothersome and time consuming. Some products feature the rip-away side system to remove the garment. With these products, however, it is necessary to undress the child from the waist down to change to a new garment.

While the crotch area of a diaper or training pant typically receives all of the excrement and urine emitted from the toddler, there are other areas that are unused for the absorption and collection process, and are used primarily only to hold the diaper in place. For example, the area of the garment about the waist, the hips and the upper portion of the buttocks are often unsoiled during diaper use, and when it is removed and discarded, a substantial amount of unused material is discarded, and must be disposed of along with the other, used areas of the diaper or training pant. Further, the provision of such large diapers or training pants, a portion of each which is not used for absorption and collection purposes, requires the undergarment to be larger and more expensive to produce, and more expensive to dispose of than would be a product of the size and shape necessary only to collect and contain the excrement of the toddler.

While the foregoing undergarment changing procedure for a child generally has become accepted as necessary in today's society, there still is a need for a more expedient method of changing the absorbent garment of a small child, without unnecessary use and waste of materials and without the requirement of removing so many garments from the toddler or small child in the change-over process.

The new invention, the disposable or reusable garment with the disposable liner/diaper, is constructed in an effort to meet all of the objectives. This product is designed to open at the lower front abdomen section of the garment gaining access to an open crotch for two reasons. First, there is an optional disposable liner/diaper that can be used for added protection. It can be removed and replace without having to remove the garment. Second, a new garment can be changed, if necessary. Using the optional disposable liner/diaper in conjunction with the disposable or reusable garment will give the ability to minimize diaper or training pant waste, and will reduce the cost of expensive disposable garments.

The universal disposable liner/diaper is unique in that it will fit into the training pants described herein, and can also be worn in any regular toddler's or children's undergarment, infant diaper cover, or on the inside of a conventional cloth diaper. The wear and tear on conventional cloth diaper or cloth garments will be substantially decreased, and the cost of garment replacement will decrease.

It is the purpose of this invention to provide a more healthy, sanitary, user-friendly environment for both the parents and the child in one of the most demanding, but natural stages of the child's life. It is also our intention to give the consumer, at all income levels, the opportunity to afford a training system that can meet their needs, without sacrificing the features of the invention capabilities.

SUMMARY OF THE INVENTION

Briefly described, the present invention comprises a disposable or reusable garment in the form of training pants or briefs with a disposable liner that is suitable for use by an incontinent person, such as a child in its early years during its toilet training phase. The invention includes a garment featuring a lower front separating system which receives an absorbent liner that functions as a diaper, and the garment can be opened without removal of the garment from about the waist of the toddler while removing the soiled liner and its contents, and placing a fresh liner in the garment.

The garment is absorbent and is applied to the lower abdomen of a person and includes a reusable undergarment and a replaceable absorbent disposable liner/diaper. The reusable undergarment includes a continuous waistband structure adapted to completely encircle a waist of the person, the waistband structure having an inside surface for facing the person, and having a back segment, a top front segment and opposed side segments. A releasable panel extends from the back segment of the waistband structure and forms a crotch segment for extending about the crotch of a person, and a front abdominal segment extends from the crotch segment toward the top front segment of the waistband structure and has an upper end portion having an outside surface for placement in underlying engagement with the inside surface of the top front segment of the waistband structure.

Pressure sensitive connectors extend along the outside surface of the upper end portion of said front abdominal segment of said releasable panel and along the inside surface of the top front panel of the waistband structure for releasably connecting the upper end portion of the front abdominal segment of the releasable panel to the inside surface of the top front segment of the waistband structure to form leg openings of the garment.

The absorbent disposable liner/diaper includes a liquid impermeable outer layer of sheet material for placement facing the releasable panel of said undergarment, a liquid permeable outer layer of sheet material opposed to said liquid impermeable outer layer of sheet material for placement facing the person, and intermediate layers of liquid absorbent material confined between said outer layers of sheet material.

The absorbent disposable liner/diaper is in the shape of an approximate hourglass with a narrow intermediate crotch portion sized for placement adjacent the crotch segment of the releasable panel and opposed end portions wider than the intermediate crotch portion sized for placement adjacent the back segment and the front abdominal segment of the releasable panel. The absorbent disposable liner/diaper is of a length sufficient to extend from the back segment of the waistband structure to the upper end portion of the releasable panel, and is supported by said releasable panel and is releasable with said releasable panel with respect to said top front segment of the waistband structure.

The liner/diaper is directly supported by the releasable panel so that the liner/diaper is movable with said releasable panel such that the liner/diaper and panel are adapted to move toward and away from the crotch of the person.

When the garment is worn by a person, the front abdominal segment of the releasable panel can be released from the top front segment of the waistband structure to open the front abdominal segment and crotch segment of the releasable panel and the disposable liner/diaper can be moved with the front abdominal segment to expose the crotch of a person and the disposable liner/diaper can be removed from the undergarment and another duplicate disposable liner/diaper can be inserted into position in the undergarment and connected to the releasable panel and the front segment reconnected to the top front segment of the undergarment, without removing the undergarment from the person.

Thus, it is the objective of this invention to provide an improved garment for a child to use which absorbs and contains the excrement of the child, while providing quick removal, clean up, and replacement of a new liner/diaper during the toilet training phase.

Other objectives, features and advantages of the present invention will become apparent upon reading the following specifications, when taken in conjunction with the accompanying drawings.

BRIEF DESCRIPTION OF THE DRAWINGS

FIG. 1 is a perspective view of the toddler's garment, showing the releasable panel in its connected position, with a portions of the waistband and leg bands removed to show the elastic insertions.

FIG. 2 is a perspective illustration of the garment similar to FIG. 1, but showing the releasable panel opened away from the upper front panel, and the disposable liner/diaper in overlaying relationship with respect to the releasable lower front panel.

DETAILED DESCRIPTION

Figure 3:
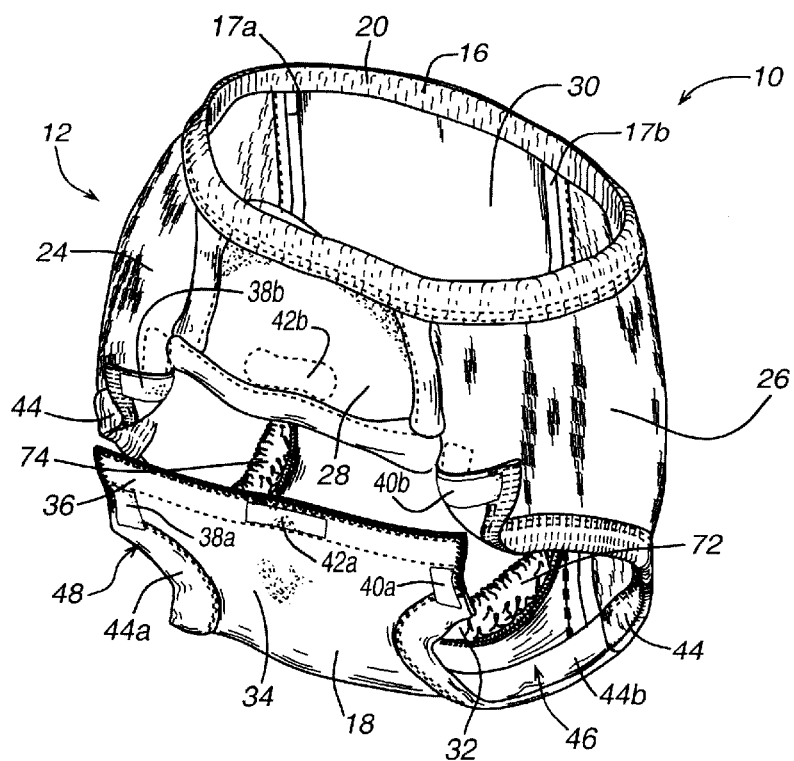
FIG. 3 is a perspective illustration, similar to FIG. 1, but showing the releasable upper top panel in a position where the connectors of the lower front panel are illustrated, and showing the corners of the hip panels turned upwardly to expose the mating elements of the releasable connectors.

Referring now in more detail to the drawings, in which like numerals indicate like parts throughout the several views, FIG. 1 illustrates the toddler's garment 10 in the form of briefs or toilet training underpants which include an undergarment 12 and a disposable liner 14. Undergarment 12 has a waistband structure 15 that includes a waistband 16 for surrounding the waist and hips of the toddler, and a releasable panel 18 that extends from the front of the waistband structure, downwardly through the crotch area of the garment, and upwardly toward the back of the waistband structure.

The waistband structure 15 includes a waistband 16 having an outer fold or sheath of soft stretchable cotton which encloses an adjustable band of elastic 22 for completely encircling the waist of the toddler. The waistband structure further includes hip panels 24 and 26 connected at their upper edges to the waistband 16 and a top center front panel 28 which is connected at its side edges to the hip panels 24 and 26, and at its upper edge to the waistband 16. The hip panels 24 and 26 are each connected at their rear edges to the back segment 30 by impervious strips 17a and 17b. With this arrangement, it can be seen that the hip panels 24 and 26 form opposed side segments of the waistband structure, the top front panel 28 forms a front segment of the waistband structure, and the upper back segment 30 forms the back segment of the waistband structure.

As best shown in FIG. 2, the releasable panel 18 extends from the back segment 30 for placement adjacent the buttocks of the toddler. The releasable panel includes a crotch segment 32 for extending about the crotch of the toddler, and a front segment 34 for extending from the crotch segment toward the front panel 28. The front segment 34 of the releasable panel 18 includes an upper end portion 36 for placement in underlying engagement with the inside surface of the front panel 28.

As shown in FIG. 3, cooperative connector elements are carried by the front segment 34 of the releasable panel 18. In the illustrated embodiment, hook and loop connectors are used, with hook fasteners 38a, 40a and 42a attached at the front segment 34 of the disposable or reusable garment. The hook fasteners 38a, 40a and 42a are placed on the outwardly facing surface of the releasable panel 18, whereas the mating loop connectors 38b, 40b and 42b are mounted on the inwardly facing surfaces of the top front panel 28 and hip panels 24 and 26. With this arrangement, the upper end portion 36 of the front segment 34 will be placed in underlying relationship with respect to the front panel 28 with the front panel 28 covering the upper end portion 36, so that the releasable panel 18 is less likely to be inadvertently released from the front panel 28, and hip panels 24 and 26 of the disposable or reusable garment. With this arrangement, the entire absorbent side of the disposable liner/diaper is positioned in a facing relationship with respect to the toddler.

The lower edges of the hip panels 24 and 26 and the opposed edges of the releasable panel 18 are formed with overedge binding 44, so that the leg openings 46 and 48 are completely surrounded by the overedge binding. Encased inside the overedge binding in the crotch area 32 is a section of elastic on opposed sides 44a and 44b for adjustable leg openings.

Typically, the releasable panel 18 of the reusable garment will be fabricated of multiple layers of soft cotton knit fabric, with the exterior layer being of liquid impervious fabric such as a durable vinyl. In another embodiment of the invention the releasable panel 18 will not include the outer layer of vinyl. In this reusable embodiment of the invention, the entire garment will be made primarily of soft cotton knit. This allows the absorbent cotton knit layers of the releasable panel to absorb liquid, but the liquid impervious binding 44 serves to block the liquid and retain it in the more absorbent cotton layers, to avoid leakage.

The releasable panel 18 in the disposable garment will be made from non-woven, absorbent fabric layers on the inside of the releasable panel 18, and a non-woven impervious layer on the exterior of panel 18. With this arrangement of layers of fabric, should the excrement of the toddler exceed the capacity of the liner, the garment will function to absorb and contain the excess excrement. Moreover, the fabric facing the toddler is absorbent, smooth and comfortable so as to not chafe the toddler. The binding 44 that forms the leg openings 46 and 48 of the garment will be of liquid impervious fabric.

In the cotton knit garment, the side panels 24 and 26 are made of a stretchable cotton knit fabric which is porous and allows the skin of the toddler to breathe through the fabric. The disposable garment side panels are made from a porous non-woven fabric that is also a breathable fabric for comfort for the toddler.

In the reusable garment the upper center front panel 28 is made of soft cotton knit fabric on the interior and a layer of liquid impervious fabric on the exterior. This vinyl fabric stabilizes the positions of the hook and loop connectors 38b, 40b, and 42b, so that the stretching of the garment will not disrupt the positions of the hook and loop connectors, as well as adding protection to the top front panel.

The side hip panels 24 and 26 are connected to back segment 30 with strips of liquid impervious fabric 17a and 17b approximately 1 ¼" wide. A heat sealed seam extends down the center of the strip to create a liquid barrier between the back segment 30 and the hip panels 24 and 26. The strips 17a and 17b are stitched to adjoining panels 24, 26 and 18 (on opposed sides) on the reusable garment and sonic bonded to the adjoining panels on the disposable garment.

Figure 4:
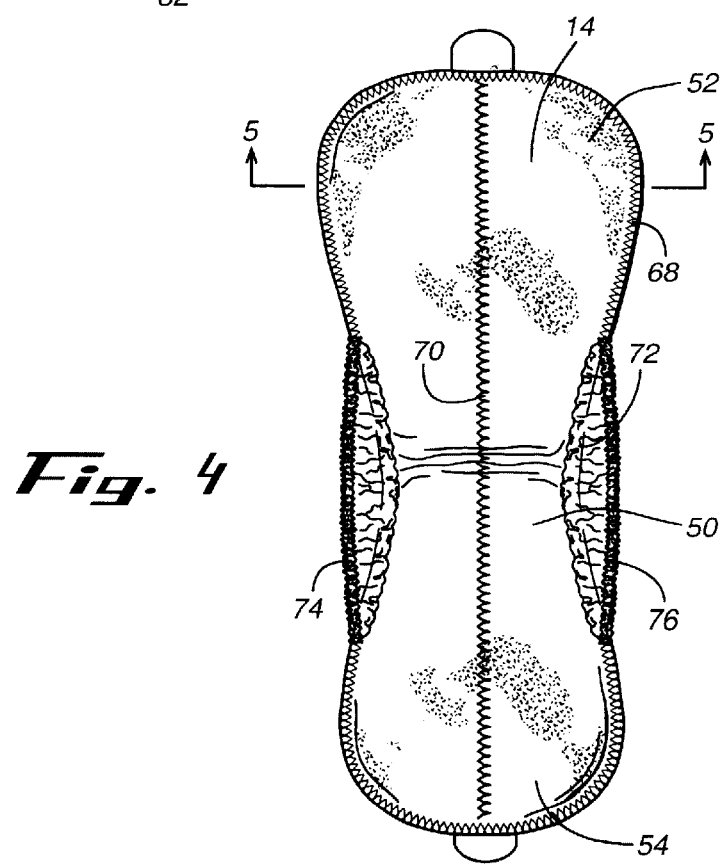
FIG. 4 is a plan view of the disposable liner/diaper.
Figure 5:
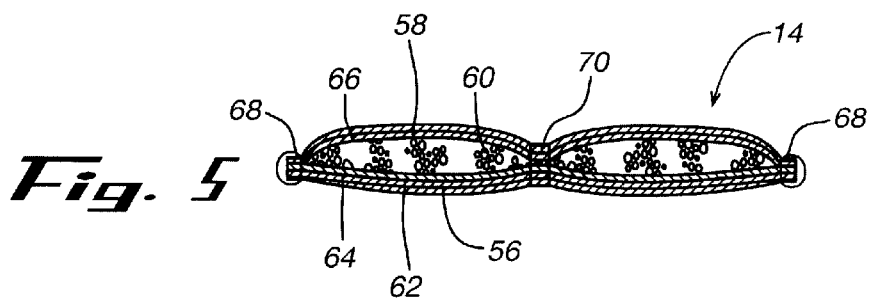
FIG. 5 is a cross-sectional view of the disposable liner/diaper, taken along lines 5—5 of FIG. 4.
Figure 6:
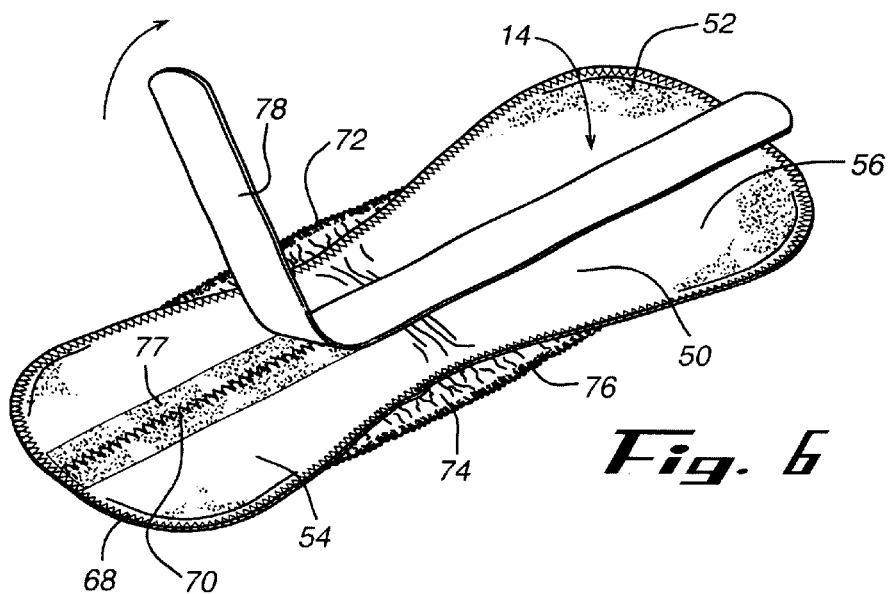
FIG. 6 is a perspective illustration of the back of the disposable liner/diaper, showing the band of adhesive on the back of the liner/diaper, and the protective strip partially removed from the bank of adhesive.

As illustrated in FIGS. 4–6, the disposable liner/diaper 14 is substantially flat and has an hourglass configuration, which includes a relatively narrow intermediate crotch portion 50 which is sized and shaped to be received adjacent the crotch panel segment 32 of the releasable panel 18, and enlarged opposed end portions 52 and 54 which are wider than the intermediate crotch portion 50 which is sized for placement adjacent the back segment 30 and the front segment 34 of the garment. The disposable liner/diaper is of an overall length adequate to extend from overlaying relationship with respect to the back segment 30 down from the waistband 16, then downward adjacent the crotch panel segment 32, and then upward adjacent the lower front panel segment 34, so as to cover the buttocks, crotch and lower front abdomen of the toddler. The toddler's garment is constructed so that the back segment 30 and the releasable panel 18 receive and support the entire length of the liner 14.

As illustrated in FIG. 5, the disposable liner/diaper 14 is fabricated of multiple layers of non-woven fabric. A liquid impermeable layer made from vinyl fabric is used as the outer layer 56 that faces away from the toddler and toward the back segment 30 and releasable panel 18, and a liquid permeable non-woven soft absorbent layer 58 faces the toddler. Granular or powdered liquid absorbent particles 60, are positioned between the two inner layers of non-woven fabric 64 and 66, to retain the particles within the confines of the liner/diaper. A non-woven absorbent core 62, is used so as to stabilize the liner/diaper. The aligned edges of the layered fabrics 56, 58, 62, 64, and 66 are bound together by a sonic bonded edge 68.

A bonded, or heat sealed seam 70, is formed intermediate the side edges of the liner/diaper, extending along the length of the liner/diaper, from one enlarged end portion 54. The seam evenly distributes the loose absorbent particles 60, on each side of the bonded seam. The seam 70 creates a space in the liner/diaper for fluids to flow toward the center, locking in moisture, away from the edge. This assures that the moisture being pulled toward the center seam 70 will automatically be evenly distributed over the crotch area 50 to avoid becoming "bunched" into one portion of the liner/diaper 14.

As illustrated in FIGS. 4 and 6, liquid impermeable wings 72 and 74 are bonded to the crotch portion 50 of the liner/diaper 14, by bonded edge 68. The wings include an elastic border 76, so that the wings tend to form a trough for the collection of excrement emitted by the toddler.

As illustrated in FIG. 6, the liquid impermeable layer 56 of the liner/diaper is coated with a band of adhesive 77, from end to end of the liner/diaper, and a protective strip 78 is applied to the band, to cover the adhesive. When the liner 14 is to be placed in the toddler's garment 12, the strip 78 is removed from the adhesive 77, and the liner is place so that the adhesive faces the back segment 30 and the releasable panel 18, causing the liner/diaper to cling to the back segment and panel. The panel 18 is then attached to the interior of the top center front panel 28, with the end portion 36 of the releasable panel 18 tucked inside the panel 28. This places the entire absorbent surface of the liner/diaper 14 into contact with the toddler, and usually avoids having any absorbent surface of the liner/diaper in contact with the outer garment.

Figure 7:
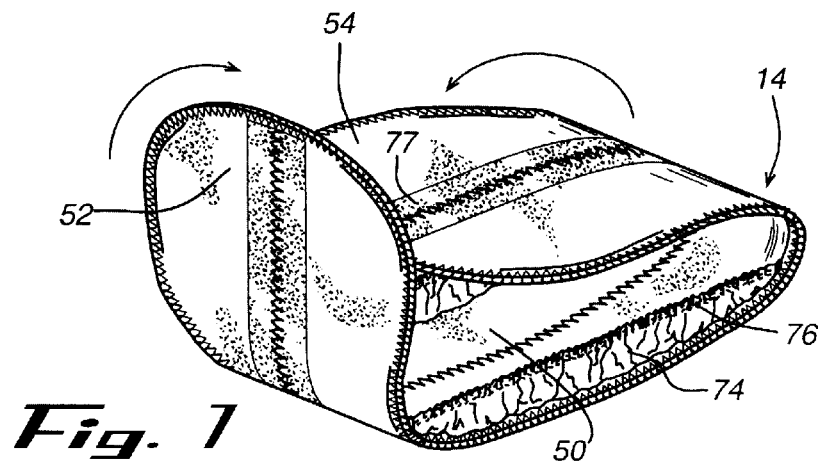
FIG. 7 is a perspective illustration of the disposable liner/diaper, showing how the enlarged ends of the liner/diaper are folded over the intermediate crotch area of the liner to contain the excrement from the toddler.
Figure 8:
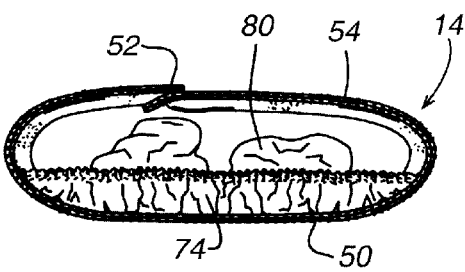
FIG. 8 is a side elevation view of the disposable liner/diaper, in its folded over position, containing excrement, with the adhesive from one end adhered to the opposite end to hold excrements inside.

When the liner 14 is removed from the garment, the liner can be folded as shown in FIG. 7, so that its ends are arranged in overlying relationship, and one end of the liner/diaper overlays and is pressed against the other end of the liner/diaper, against the adhesive band 77. This causes the ends of the liner/diaper to cling to one another, as illustrated in FIG. 8. Further, the wings 72 and 74 of the liner/diaper tend to form side walls in the folded over liner/diaper, thereby tending to contain the excrement 80 within the liner/diaper, for safe disposal of the excrement.

Although the invention has been disclosed as to be used by toddlers during their toilet training stage, the invention can be used by other incontinent people.

While preferred embodiments of the invention have been disclosed in detail in the foregoing description and drawings, it will be understood by those skilled in the art that variations and modifications thereof can be made without departing from the spirit and scope of the invention as set forth in the following claims.

What is claimed is:

1. An absorbent garment for a lower abdomen of a person comprising a reusable undergarment and a replaceable absorbent disposable liner/diaper, said undergarment including:

a continuous waistband structure adapted to completely encircle a waist of the person, said waistband structure having an inside surface for facing the person, and having a back segment, a top front segment and opposed side segments;

a releasable pane extending from said back segment of said waistband structure and forming a crotch segment for extending about a crotch of the person, and a front abdominal segment for extending from said crotch segment toward the top front segment of said waistband structure and having an upper end portion for placement in underlying engagement with the inside surface of the top front segment of said waistband structure;

pressure sensitive connector means extending along said upper end portion of said front abdominal segment of said releasable panel and along said top front segment of said waistband structure for releasably connecting the upper end portion of said front abdominal segment of said releasable panel to the inside surface of the top front segment of said waistband structure to form leg openings of the garment;

said absorbent disposable liner/diaper comprising:

a liquid impermeable outer layer of sheet material for placement facing the releasable panel of said undergarment, a liquid permeable outer layer of sheet material opposed to said liquid impermeable outer layer of sheet material for placement facing the person, and intermediate layers of liquid absorbent material confined between said outer layers of sheet material;

said absorbent disposable liner/diaper being of an approximate hourglass-shape with a narrow intermediate crotch portion sized for placement adjacent said crotch segment of said releasable panel and opposed end portions wider than said intermediate crotch portion sized for placement adjacent the back segment and the front abdominal segment of said releasable panel and being of a length sufficient to extend from said back segment of said waistband structure to said upper end portion of said releasable panel;

said absorbent disposable liner/diaper being supported by said releasable panel and releasable with said releasable panel with respect to said top front segment of the waistband structure;

means for connecting said liner/diaper directly to said releasable panel so that the liner/diaper is movable with said releasable panel such that the liner/diaper and panel are adapted to move toward and away from the crotch of the person;

whereby when the garment is worn by a person, the front abdominal segment of the releasable panel can be released from the top front segment of the waistband structure to open the front abdominal segment and crotch segment of the releasable panel and the disposable liner/diaper can be moved with the front abdominal segment to expose the crotch of a person and the disposable liner/diaper can be removed from the undergarment and another duplicate disposable liner/diaper can be inserted into position in the undergarment and connected to the releasable panel and the front abdominal segment reconnected to the top front segment of the undergarment; without removing the undergarment from the person.

2. The garment of claim 1 and wherein said disposable liner/diaper further includes opposed sides and a bonded seam formed intermediate said opposed sides of the liner/diaper along the liner/diaper from one of said end portions, through said intermediate crotch portion to the other of said end portions, said bonded seam confining the layers of liquid absorbent materials in predetermined positions on opposite sides of said seam in said disposable liner/diaper.

3. The garment of claim 1 and wherein said disposable liner/diaper further includes protective wings bonded to said intermediate crotch portion, said wings having elastic edging and forming a trough for said liner/diaper for containment of excrement.

4. The garment of claim 1 and wherein said waistband structure includes an encased elastic band for surrounding the waist of the person for easy fit adjustment.

5. A garment for a lower abdomen of a person comprising reusable briefs and an absorbent replaceable liner, said briefs including:

a waistband structure adapted to completely encircle a waist of a person, said waistband structure having an inside surface for facing the person, and having a back segment, a front segment and opposed side segments;

a releasable panel extending from the back segment of said waistband structure and forming a crotch segment for extending about a crotch of the person, and a front abdominal segment for extending from the crotch segment toward the front segment of the waistband structure, said abdominal segment having an upper end portion for placement in underlying engagement with the inside surface of the front segment of said waistband structure;

connector means for releasably connecting the upper end portion of said front abdominal segment to the inside surface of the front segment of said waistband structure so that said waistband structure and said releasable panel form leg openings of the briefs;

said absorbent replaceable liner comprising:
 a liquid impermeable outer layer of sheet material for placement facing the releasable panel of said briefs, a liquid permeable outer layer of sheet material opposed to said liquid impermeable outer layer of sheet material for placement facing the person, and an intermediate layer of liquid absorbent material confined between said outer layers of sheet material;
 said liner being of an approximate hourglass-shape with a narrow intermediate portion sized for placement adjacent said crotch segment of said releasable panel, and opposed end portions wider than said intermediate portion sized for placement adjacent said back segment and said front segment of said briefs;
 said liner being of a length adequate to extend from adjacent the back segment of said waistband structure adjacent the crotch segment to a position adjacent the upper end portion of said front abdominal segment so as to cover the buttocks, a crotch and a lower front abdomen of a person when worn;
 said liner being positioned in overlying relationship with said releasable panel for placement about the buttocks, the crotch and the front abdomen of the person;

whereby when the garment is worn by the person, the upper end portion of the front segment of the releasable panel can be released from the front segment of the waistband structure of the briefs to open the front abdominal segment and crotch segment of the briefs and the liner away from the front segment of the waistband structure and the liner can be inspected and removed from the briefs, and another duplicate liner can be inserted into position in the briefs and the upper end portion of the front segment of the releasable panel reconnected to the inside surface of the front segment of the waistband structure, without removing the briefs from the person.

6. A garment for an incontinent person comprising reusable briefs and a replaceable absorbent liner, said briefs including:

a waistband structure adapted to completely encircle a waist of the person, said waistband structure having an inside surface for facing the person, and having a back waistband segment for placement about a back of the person, a front waistband segment for placement about a lower front abdomen of the person and opposed side waistband segments for placement at hips of the person, a releasable panel extending from said back waistband segment of said waistband structure and forming a crotch segment for extending about a crotch of the person, and a front segment for extending from said crotch segment toward said front waistband segment of said waistband structure and having an upper end portion for placement in underlying engagement with the inside surface of said front waistband segment of said waistband structure;

connector means for releasably connecting said upper end portion of said front segment of said releasable panel to the inside surface of said front waistband segment of said waistband structure so that said waistband structure and said releasable panel form leg openings of the briefs;

said liner being of an approximate hourglass shape with a narrow intermediate portion sized for placement adjacent said crotch segment of said releasable panel and opposed end portions wider than said intermediate portion sized for placement adjacent said back segment and said front segment of said releasable panel;

said liner being of a length adequate to extend from said back waistband segment of said waistband structure to said upper end portion of said releasable panel and cover a buttocks, the crotch and a lower front abdomen of the person when worn;

adhesive means applied to said liner for adhering said liner to said releasable panel with said liner supported by said releasable panel and movable with said releasable panel with respect to said front waistband segment of the waistband structure;

whereby when the garment is worn by the person, the front segment of the releasable panel can be released from the front waistband segment of the waistband structure of the briefs to open the front segment and crotch segment of the releasable panel and the liner can be removed from the briefs, and another duplicate liner can be inserted into position in the briefs, and the front segment of the releasable panel reconnected to the front waistband segment of the waistband structure, without removing the briefs from the person.

* * * * *